(12) United States Patent
Akhavan et al.

(10) Patent No.: US 11,571,438 B1
(45) Date of Patent: Feb. 7, 2023

(54) NUTRACEUTICAL COMPOSITIONS TO UP-REGULATE SIRT1 AND METHODS OF USE

(71) Applicants: Sasan Akhavan, Porter Ranch, CA (US); Amir Hayeri, West Vancouver (CA)

(72) Inventors: Sasan Akhavan, Porter Ranch, CA (US); Amir Hayeri, West Vancouver (CA)

( * ) Notice: Subject to any disclaimer, the term of this patent is extended or adjusted under 35 U.S.C. 154(b) by 0 days.

(21) Appl. No.: 17/751,269

(22) Filed: May 23, 2022

(51) Int. Cl.
*A61K 31/7084* (2006.01)
*A61K 47/10* (2017.01)
*A61K 9/00* (2006.01)
*A61K 45/06* (2006.01)

(52) U.S. Cl.
CPC ........ *A61K 31/7084* (2013.01); *A61K 9/0053* (2013.01); *A61K 45/06* (2013.01); *A61K 47/10* (2013.01)

(58) Field of Classification Search
CPC ... A61K 31/7804; A61K 47/10; A61K 1/7804
See application file for complete search history.

(56) References Cited

U.S. PATENT DOCUMENTS

| | | | |
|---|---|---|---|
| 10,695,360 B2 | 6/2020 | Yoshino et al. | |
| 11,013,710 B2 | 5/2021 | Dhamane et al. | |
| 2018/0050054 A1* | 2/2018 | Imai | A61P 43/00 |
| 2021/0346365 A1 | 11/2021 | Baur et al. | |

OTHER PUBLICATIONS

"A Critical Appraisal of Solubility Enhancement Techniques of PolyPhenols," Kaur and Kaur; Journal of Pharmaceutics; vol. 2014.
"Autophagy and senescence: A new insight in selected human diseases," Rajendran et al., Journal of Cellular Physiology, May 2019.
"Bioavailability of the Polyphenols: Status and Controversies," D'Archivio et al., Int. J. Mol. Sci. 2010, 11, 1321-1342.
"Dual Role of Autophagy in Regulation of Mesenchymal Stem Cell Senescence," Rastaldo et al., Front. Cell Dev. Biol., Apr. 24, 2020.
"Effects of Resveratrol and other Polyphenos on Sirt1: Relevance to Brain Function During Aging," Sarubbo et al., Current Neuropharmacology, 2018, 16, 126-136.
"High Levels of SIRT1 Expression as a Protective Mechanism Against Disease-Related Conditions," Elibol and Kilic, Front. Endocrinol., Oct. 15, 2018.
"Identification of the 100 richest dietary sources of polyphenols: An application of the Phenol-Explorer database," Perez-Jimenez et al., European Journal of Clinical Nutrition, Nov. 2010.
"Major Water-Soluble Polyphenols, Proanthocyanidins, in Leaves of Persimmon (Diospyros kaki) and Their a-Amylase Inhibitory Activity," Kawakami et al., Biosci. Biotechnol. Biochem., 74 (7), 13820-1385-2010.
"Polyphenols and Human Health: The Role of Bioavailability," Lorenzo et al., Nutrients 2021, 13, 273.
"Polyphenols: food sources and bioavailability," Manach et al., Am J Clin Nutr 2004; 79:727-47.
"Role of Nutraceutical SIRT1 modulators in AMPK and mTOR pathway: Evidence of synergistic effect" Giovannini and Bianchi, Feb. 2017, vol. 34, pp. 82-98.

* cited by examiner

*Primary Examiner* — Carlos A Azpuru
(74) *Attorney, Agent, or Firm* — Diament Patent Law, P.C.; Adam Diament

(57) ABSTRACT

The present invention discloses a nutraceutical composition for up-regulation of SIRT 1 expression. The nutraceutical composition comprises NMN at in an amount between 300 mg and 500 mg, in an amount of 500 mg, and a soluble agent. The NMN and polyphenol are wrapped in a soluble agent as a protective bio-active agent to increase bioavailability and protect the polyphenol compounds during gut absorption. The invention also discloses a method of preparing a nutraceutical composition by weighing polyphenol at a suitable concentration, mixing the polyphenol with a suitable soluble agent and finally adding NMN to the mixture and blended it to form the nutraceutical composition. The nutraceutical composition up regulates SIRT1 and hence is suitable for treatment of various diseases and used in the form of powder, liquid, tablets, capsules, chewable form, gels, etc.

13 Claims, No Drawings

NUTRACEUTICAL COMPOSITIONS TO UP-REGULATE SIRT1 AND METHODS OF USE

FIELD OF THE DISCLOSURE

The present invention discloses a nutraceutical composition for up-regulation of expression of SIRT1 (Sirtuin 1) enzyme. More particularly, the present invention discloses the nutraceutical composition with a specific combination of nicotinamide mononucleotide (NMN), a polyphenol and a soluble agent.

BACKGROUND OF THE INVENTION

Nicotinamide mononucleotide is a bioactive nucleotide that is most recognized for its role as an intermediate of Nicotinamide Adenine Dinucleotide (NAD+) biosynthesis. NMN is one of the main precursors of nicotinamide adenine dinucleotide (NAD+), an essential enzyme for various critical cell functions, including metabolism, Deoxyribonucleic acid (DNA) repair, cell growth and survival.

NMN is associated with increased NAD+ biosynthesis, suppressed age-related adipose tissue inflammation, enhanced insulin secretion and insulin action, improved mitochondrial function, and improved neuronal function in the brain.

NMN levels decrease with age, and aging itself has also been shown to significantly compromise the body's conversion of NMN to NAD+. NMN has been able to suppress age-associated weight gain, enhance energy metabolism and physical activity, improve insulin sensitivity, improve eye function, improve mitochondrial metabolism and prevent age-linked changes in gene expression.

Polyphenols are a large family of naturally occurring organic compounds characterized by multiples of phenol units. Polyphenols are found in plants, including flavonoids and phenolic acid that greatly benefit the human body and help fight disease. Polyphenols are now widely considered to play an important role in maintaining health and well-being throughout the body, mainly as a result of their antioxidant activity.

SIRT1, which is encoded by the SIRT1 gene is the most conserved mammalian nicotinamide adenine dinucleotide (NAD+) dependent histone deacetylase. Besides its role being a target for histone and non-histone proteins, SIRT1 functions as a transcription factor for many different physiological processes.

Resveratrol is a polyphenol with major health benefits that is thought to operate through direct activation of NAD+ levels thus up regulating SIRT1. SIRT1 requires NAD+ as a substrate to perform its gene silencing function, higher NAD+ levels enhances SIRT1 activity. Thus, resveratrol promotes SIRT1 function by enhancing NAD+ synthesis in whole cell systems without requiring direct activation.

Generally, polyphenols show a low bioavailability due to several factors such as interaction with the food matrix, the metabolic processes mediated by the liver, intestine and microbiota. As polyphenol bioavailability is influenced by food matrix components, specific strategies could be considered in order to increase their in vivo delivery such as fermentation or exploiting the association among foods, or to protect them from degradation such as microencapsulation.

SIRT1 is a nicotinamide adenosine dinucleotide (NAD)-dependent deacetylase that removes acetyl groups from various proteins. SIRT1 performs a wide variety of functions in biological systems. SIRT1 is an important regulator of energy homeostasis in response to nutrient availability.

SIRT1 activates mitochondrial signals and pathways regulating the expression levels of genes crucial for proliferation and ATP generation. SIRT1 increases mitochondrial biogenesis thereby contributing to increased healthy lifespan and reducing aging-related diseases. SIRT 1 enzymes are indirectly responsible for DNA deacetylation and directly responsible for regulating cell senescence, autophagy, and apoptosis.

SIRT1 takes a part in chronic inflammation, its expression levels and protein levels are reduced in several chronic inflammatory diseases such as arterial inflammation, obesity, and Alzheimer's disease. In addition, chronic inflammation is associated with increased NFκB RelA/p65 activity secondary to decreased SIRT1.

Nutraceuticals are compositions that do not fall neatly into the categories of pure vitamins, amino acids or herbal remedies. These compositions are generally products derived from food sources that have extra health benefits in addition to the basic nutritional value found in foods used that improve health, delay the aging process, prevent chronic diseases, increase life expectancy, or support the structure or function of the body.

Currently, nutraceuticals have received considerable interest due to potential nutritional, safety and therapeutic effects. Over the past several years, the ever-growing awareness that good health goes hand-in-hand with a healthy and balanced diet has encouraged people to eat more fruit and vegetables, and to take supplements to make up for nutritional deficiencies.

Natural polyphenols are the largest group of phytonutrients and are considered potential agents for the prevention and treatment of stress-related oxidative diseases. They are found in many plants and foods, such as fruits, vegetables, tea, cereals, and wine, and long-term intake is associated with health benefits. Mediterranean diets are in fact linked to a reduced risk of chronic diseases due to the consumption of olive oil and red wine, which contain high amounts of polyphenols U.S. Patent Publication No. US20210346365A1 entitled "Methods for enhancing liver regeneration" discloses methods, kits, and pharmaceutical compositions for enhancing liver regeneration in a mammal in need thereof, comprising administering a therapeutically effective amount of an agent that increases nicotinamide adenine dinucleotide (NAD) activity. The methods may include administering a therapeutically effective amount of an agent that increases nicotinamide adenine dinucleotide (NAD) activity and a sirtuin 1 (Sirt1) agonist. The agent that increases NAD activity may be a NAD precursor. The NAD precursor may include one or more of tryptophan, nicotinic acid, nicotinic acid riboside, nicotinamide riboside (NR), nicotinamide, NADP, and NAD itself, and a pharmaceutically acceptable salt thereof.

U.S. Patent publication No. US20180050054A1 entitled "Administration of Nicotinamide Mononucleotide in the Treatment of Disease" discloses methods and compositions related to methods of treating, ameliorating, mitigating, slowing, arresting, preventing or reversing various diseases and conditions, including age-related obesity, age-related increases in blood lipid levels, age-related decreases in insulin sensitivity, age-related decreases in memory function, and age-related changes in eye function such as macular degeneration. The methods comprise administering nicotinamide mononucleotide (NMN) to a subject. In some embodiments, the administration can be oral administration.

The Publication entitled "*Role of nutraceutical SIRT1 modulators in AMPK and mTOR pathway: Evidence of a synergistic effect*" to Giovannini and Biachi in *Nutrition*, discloses the effect of different natural substances on SIRT1 expression and on AMPK and mTOR phosphorylation and the synergistic effect between the substances. The results indicate that the expression of SIRT1 was significantly increased in all experimental groups compared with the control group (p<0.001). In addition, the simultaneous administration involved a significant and synergistic increase in the expression of SIRT1 for some but not all of the tested compounds. Finally, the individual administration of berberine, quercetin, ferulic acid, and tyrosol resulted in a statistically significant increase in AMPK activation and mTOR inhibition.

BRIEF SUMMARY OF THE PRESENT INVENTION

Even though there are available compositions with combination of NMN with polyphenol, there is no combination, which exhibits synergistic effect in up regulation of SIRT1. Hence, there is a need for nutraceutical composition with a specific combination of ingredients, which exhibits synergistic effect in up-regulation of expression of SIRT1.

The present invention features nutraceutical composition for up regulation of SIRT 1 expression. The nutraceutical composition is a combination of specific compounds and embodiments having specific concentrations.

In one aspect of the present invention, there is provided a composition having NMN, a polyphenol, and a soluble where NMN and the polyphenol are wrapped in a protective bio active agent to increase bioavailability and protect the agent. The invention provides nutraceutical composition comprising NMN at a concentration in a range between 300 mg and 500 mg, a polyphenol at a concentration of 500 mg and a soluble agent. The compounds NMN, polyphenol are wrapped in a soluble agent as a protective bio-active agent to increase bioavailability and protect the polyphenol compounds during gut absorption.

The nutraceutical composition comprises polyphenol and is selected from quercetin, fisetin, bromelain, capsaicinoids, lignans, stilbenes and trans-resveratrol. Polyphenols are associated with low bioavailability and this is resolved by the use of specific combination with NMN and the soluble agent.

The soluble agent is selected based on the polyphenol selected and are selected from a group comprising olive oil, yogurt, fenugreek oil, caffeine and red wine. The nutraceutical composition with a combination of the compounds NMN, polyphenol and the soluble agent exhibit synergistic effect to enhance the expression of SIRT1.

The nutraceutical composition of the present invention is prepared in various forms such as powder, liquid, tablets, capsules, chewable form, gels etc. and is suitable and compatible for consumption.

The present invention also discloses a method for preparation. In another aspect of the invention, the method comprises the steps of weighing polyphenol at a suitable concentration, mixing the polyphenol with a suitable soluble agent. Finally, NMN is added to the mixture and blended to form the nutraceutical composition.

The combination of NMN, polyphenol and soluble agent results in synergistic effect in up-regulation of SIRT1. The nutraceutical composition of the present invention is safe and effective up-regulation of SIRT1 expression and is prepared in multiple forms suitable for safe and compatible consumption with inducing any side effects.

DETAILED DESCRIPTION OF EMBODIMENTS

The invention now will be described more fully hereinafter, in which embodiments of the invention are described. This invention may however be embodied in many different forms and should not be construed as limited to the embodiments set forth herein. Rather, these embodiments are provided so that this disclosure will be thorough and complete, and will fully convey the scope of the invention to those skilled in the art.

As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section.

It will be understood that the elements, components, regions, layers and sections depicted in the figures are not necessarily drawn to scale.

The terminology used herein is for the purpose of describing particular embodiments only, and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. The numbers, ratios, percentages, and other values may include those that are ±5%, ±10%, ±25%, ±50%, ±75%, ±100%, ±200%, ±500%, or other ranges that do not detract from the spirit of the invention. The terms about, approximately, or substantially may include values known to those having ordinary skill in the art. If not known in the art, these terms may be considered to be in the range of up to ±5%, ±10%, or other value higher than these ranges commonly accepted by those having ordinary skill in the art for the variable disclosed. Thus, embodiments of the present invention should not be construed as limited to the particular shapes of regions illustrated herein but are to include deviations in shapes that result, for example, from manufacturing. The invention illustratively disclosed herein suitably may be practiced in the absence of any elements that are not specifically disclosed herein. All patents, patent applications and non-patent literature cited through this application are hereby incorporated by reference in their entireties.

When amounts are given in weights (e.g., milligrams), the relative ratios of weights compared with the weights of other compositions described in the same composition are understood to be equivalent to the weights disclosed and claimed.

In accordance with an aspect of the invention, there is disclosed a nutraceutical composition comprising a combination of NMN, a polyphenol and a soluble agent for the up-regulation of SIRT1 expression.

The nutraceutical composition of the present invention comprises a unique combination of ingredients that exhibits synergistic effect in increasing the bioavailability and up-regulation of the SIRT1 expression.

According to an embodiment of the invention, the present invention comprises NMN in an amount between 300 mg and 500 mg, a polyphenol in an amount of 500 mg and a soluble agent in an amount of 900 gm. In another embodiment, NMM is in an amount of 250 mg, resveratrol or quercetin or turmeric is an amount of 250 mg and yogurt is in an amount of 140 gm. In yet another embodiment, NMN is in an amount of 1000 mg, resveratrol or quercetin or turmeric is in an amount of 1000 mg, and yogurt is in an amount of 900 μm. In yet another embodiment, NMN is in an amount of 250 mg, fisetin is in an amount of 100 mg and yogurt is in an amount of 140 gm. Relative ratios by weight are also alternative embodiments and in relative amounts that may differ by 5%, 10%, 20%, 30%, or more. In such embodiments, a goal is to have a final product in an edible food product, such as yogurt, with a smaller dosage of resveratrol and NMN and up to a large size yogurt with a higher dosage of resveratrol and NMN. It may be useful for having constituent ingredients of resveratrol, quercetin, or turmeric to be in amounts of 1 gm (1000 mg) daily to accommodate recommended daily dosage requirements, while fisetin may only require an amount 100 mg to accommodate daily dosage recommendations, and relative amounts of other constituent ingredients likewise adjusted. The compounds NMN, polyphenol are encapsulated or enveloped in a soluble agent as a protective bio-active agent to increase bioavailability and protect the polyphenol compounds during gut absorption. This unique assembly of the ingredients enhances the bioefficacy of the composition. In addition to being encapsulated, the product may be in a two-piece capsule, soft gel, tablet (e.g. blended and compressed), or other manner that retains the constituent ingredients and compositions together.

The polyphenols used in the nutraceutical composition may be selected from a group consisting of at least one of quercetin, fisetin, bromelain, capsaicinoids, lignans stilbenes and trans-resveratrol. The polyphenols along with NMN are encapsulated using a suitable soluble agent. The soluble agents are selected based on the polyphenol used and the soluble agents are selected from a group consisting of at least one of olive oil, yogurt, fenugreek oil, caffeine, and red wine.

The unique combination of NMN, polyphenol and the soluble agent are selected to enhance the bioavailability of polyphenol, which generally possess low bioavailability.

The nutraceutical composition with a combination of the compounds NMN, polyphenol and the soluble agent exhibit synergistic effect to enhance the expression of SIRT1.

According to another embodiment, the nutraceutical composition is prepared with different combinations of polyphenol with the suitable soluble agent.

The nutraceutical composition of the present invention optionally comprises polyamines such as spermedine, spermine, and thermospermine.

In order to provide better understanding of the invention, the following examples are provided. However, the present invention is not only restricted to these examples.

Example 1: A Nutraceutical Composition in the Form of Gummies

The nutraceutical composition is prepared with various combinations of polyphenols and suitable soluble agent. In order to enhance the compatibility, the nutraceutical composition is prepared in the form of gummies. The gummies that are gelatin based and being chewable makes it as a suitable form for the nutraceutical composition. The gummies of the present nutraceutical composition comprises NMN in an amount of 50 mg, resveratrol in an amount of 100 mg and a gummy like substance (water, sugar, corn syrup, Pectin, Gelatin) in an amount in the range between 3 g-5 g. Amounts may be increased or decreased relative to each other to keep the same relative concentration of the constituent ingredients. All three ingredients are mixed and blended to obtain the nutraceutical composition in the form of gummies.

Example 2: A Nutraceutical Composition in the Form of Yogurt

The nutraceutical composition is prepared with various combinations of polyphenols and suitable soluble agent. In order to enhance the compatibility, the nutraceutical composition is prepared using yogurt. Yogurt is suitable soluble agent for the preparation of the nutraceutical composition. The nutraceutical composition comprises NMN in an amount of 500 mg, polyphenol in an amount of 1000 mg and yogurt in an amount in the range between 100 g to 500 g. Amounts may be increased or decreased relative to each other to keep the same relative concentration of the constituent ingredients. All the three ingredients are mixed and blended to obtain the nutraceutical composition and different fruits flavors shall be considered with yogurt.

In one embodiment, in a 32 oz (900 gm) of yogurt, 0.3 gm of NMN and 0.5 gm resveratrol is added to form the final amount of consumable product. Relative amounts therefore are 3000:1:1.67 of yogurt to NMN to resveratrol, by weight, respectively. Relative amounts differing by 5%, 10%, 20%, 30% or more would not detract from the spirit of the invention.

Similarly, different combinations of NMN and polyphenols are prepared using a suitable soluble agent.

The nutraceutical composition may be prepared in various forms such as powder, liquid, tablets, capsules, chewable form, gels. and are suitable and compatible for consumption.

The increased expression of SIRT1 is associated with regulation of disease related conditions such as obesity, cardiovascular diseases and neurodegeneration. The expression of SIRT1 points the importance of epigenetics in several age-related diseases. The nutraceutical composition of the present invention is capable of enhancing the expression of SIRT1.

SIRT1 up regulation is associated with multiple benefits including glucose management, neuro regenerative ability, anti-aging, mood enhancement, DNA deacetylation, cell senescence, autophagy, apoptosis etc.

The nutraceutical composition of the present invention with different combination of NMN, polyphenols and soluble agents in various forms is effective in up regulation of SIRT1.

The presence of NMN in the nutraceutical composition aids in signaling of SIRT1 and its expression and similarly the presence of the polyphenols enhances the movement and successful expression of SIRT1.

According to another embodiment, the nutraceutical composition is prepared by a method. The method comprises the steps of weighing polyphenol and mixing the polyphenol with a suitable soluble agent. Finally, NMN is added to the mixture and blended to form the nutraceutical composition. The composition is prepared at room temperature and with low humidity (e.g. between 3-5%).

The preparation of nutraceutical composition by said method results in encapsulating NMN and polyphenols in a soluble agent. This unique encapsulation enhances the stability and the bioefficacy of the nutraceutical composition.

According to a preferred embodiment, the method involves the mixing of the ingredients at a ratio of 1:0.1:150 to 1:5:600 for NMN, polyphenol and soluble agent respectively.

The combination of NMN, polyphenol and soluble agent results in synergistic effect in up-regulation of SIRT1. The nutraceutical composition of the present invention is unique and safe, as it does not contain any synthetic compounds, is effective in up-regulation of SIRT1 expression, and can be prepared in multiple forms suitable for safe and compatible consumption without inducing side effects. SIRT1 expression through the nutraceutical composition regulates glucose metabolism, DNA deacetylation, regulates various diseases and conditions thus exhibiting therapeutic effects. Current experiments have shown that enveloping resveratrol with olive oil to increase bio availability and to protect the polyphenol during gut absorption will increase serum absorptions and serum concentrations of resveratrol and ultimately increase the synergistic effects of the bio active agents after absorption.

We claim:

1. A nutraceutical composition for up-regulation of SIRT1 enzyme, the nutraceutical composition comprising:
    a) Nicotinamide Mononucleotide (NMN);
    b) a polyphenol; and,
    c) a soluble agent,
    wherein NMN and the polyphenol are wrapped in the soluble agent to protect the polyphenol during gut absorption.

2. A nutraceutical composition of claim 1, wherein NMN is in an amount between 300 mg and 500 mg, and the polyphenol is in an amount of 500 mg.

3. The nutraceutical composition of claim 1, wherein the polyphenol is selected from a group consisting of at least one of quercetin, fisetin, bromelain, capsaicinoids, lignans stilbenes and trans-resveratrol.

4. The nutraceutical composition of claim 1, wherein the soluble agent is selected from a group consisting of at least one of olive oil, yogurt, fenugreek oil, caffeine and red wine.

5. The nutraceutical composition as claimed in claimed 1, wherein the nutraceutical composition further comprises polyamines selected from a group consisting of at least one of spermidine, spermine, and thermospermine.

6. The nutraceutical composition as claimed in claimed 1, wherein NMN and the polyphenol are encapsulated in the soluble agent, thereby enhancing the stability and bioefficacy of the nutraceutical composition.

7. The nutraceutical composition of claim 1, wherein NMN, the polyphenol and the soluble agent has a ratio in an amount of 1:0.1:150 to 1:5:600, respectively.

8. The nutraceutical composition of claim 1, wherein nutraceutical composition is in the form of at least one of a powder, a liquid, a tablet, a capsule, a chewable form, and a gel.

9. A method for preparing a nutraceutical composition, the method comprising the steps of:
    a) mixing together and blending: i) Nicotinamide Mononucleotide (NMN), ii) a polyphenol, and iii) a soluble agent.

10. The method of claim 9, wherein the polyphenol is in an amount of 500 mg.

11. The method of claim 9, wherein the soluble agent selected from a group consisting of at least one of olive oil, yogurt, fenugreek oil, caffeine and red wine.

12. The method of claim 9, wherein NMN is in an amount of between 300 mg and 500 mg.

13. The method of claim 9, wherein the ratio of NMN, the polyphenol and the soluble agent is between 1:0.1:150 to 1:5:600, respectively.

* * * * *